United States Patent
Chaudhury (10) Patent No.: US 11,884,556 B2
(45) Date of Patent: Jan. 30, 2024

(54) LIQUID, AIR, AND SURFACE TREATMENT USING HIGH INTENSITY BROAD-SPECTRUM PULSED LIGHT

(71) Applicant: Aruna Inovation LLC, Bayonne, NJ (US)

(72) Inventor: Ameet Chaudhury, Bayonne, NJ (US)

(73) Assignee: ARUNA INOVATION LLC, Bayonne, NJ (US)

( * ) Notice: Subject to any disclaimer, the term of this patent is extended or adjusted under 35 U.S.C. 154(b) by 364 days.

(21) Appl. No.: 16/899,128

(22) Filed: Jun. 11, 2020

(65) Prior Publication Data

US 2021/0387868 A1 Dec. 16, 2021

(51) Int. Cl.
| | | |
|---|---|---|
| C02F 1/32 | (2023.01) | |
| C02F 1/00 | (2023.01) | |
| A61L 9/20 | (2006.01) | |
| A61L 2/24 | (2006.01) | |

(Continued)

(52) U.S. Cl.
CPC ............... *C02F 1/325* (2013.01); *A61L 2/10* (2013.01); *A61L 2/24* (2013.01); *A61L 9/20* (2013.01); *C02F 1/004* (2013.01); *C02F 1/505* (2013.01); *A61L 2202/11* (2013.01); *A61L 2202/122* (2013.01); *A61L 2202/14* (2013.01); *A61L 2209/111* (2013.01); *A61L 2209/12* (2013.01); *A61L 2209/14* (2013.01); *C02F 2201/326* (2013.01); *C02F 2201/3228* (2013.01); *C02F 2303/04* (2013.01)

(58) Field of Classification Search
None
See application file for complete search history.

(56) References Cited

U.S. PATENT DOCUMENTS

| | | |
|---|---|---|
| 6,447,720 B1 | 9/2002 | Horton, III et al. |
| 9,011,697 B2 | 4/2015 | Campbell et al. |

(Continued)

FOREIGN PATENT DOCUMENTS

| | | | |
|---|---|---|---|
| CA | 2336524 | 11/2000 | |
| CN | 1413297 A | * 4/2003 | .............. C02F 1/325 |

OTHER PUBLICATIONS

Office Action issued for Indian Patent Application No. 202044038581, dated May 31, 2022, 5 pages.

*Primary Examiner* — Andrew Smyth
(74) *Attorney, Agent, or Firm* — Hamre, Schumann, Mueller & Larson, P.C.

(57) ABSTRACT

Liquid, air, or surface treatment/sterilization/disinfection using pulsed light to eliminate, reduce, degrade, render inert, or nullify physical, chemical, biological, microbiological, or non-microbiological contaminants is disclosed herein. The system also includes at least one power supply powering the light source of the reactor, an ionized wire wrapped outside the light source of the reactor, at least one digital multiplexer connected to the at least one power supply, and a controller to control the at least one digital multiplexer to power the light source to strobe the pulsed light at a predetermined fluence, a predetermined pulsed width, and a predetermined frequency or spectrum to eliminate, reduce, degrade, render inert, or nullify the physical, chemical, biological, microbiological, or non-microbiological contaminants in a liquid flow, air, or surface at a molecular level.

19 Claims, 10 Drawing Sheets

(51) Int. Cl.
    *A61L 2/10*     (2006.01)
    *C02F 1/50*     (2023.01)

(56) References Cited

U.S. PATENT DOCUMENTS

2007/0151905 A1 * 7/2007 Wang ............... C02F 1/325
                                                210/97
2007/0247080 A1 * 10/2007 Tipton ............... H05B 41/30
                                                315/209 M
2009/0084734 A1 * 4/2009 Yencho ............... C02F 1/325
                                                210/243

* cited by examiner

Fig. 3F

US 11,884,556 B2

LIQUID, AIR, AND SURFACE TREATMENT USING HIGH INTENSITY BROAD-SPECTRUM PULSED LIGHT

FIELD OF THE DISCLOSURE

The present disclosure is generally related to treating, purifying, disinfecting, or sterilizing liquid, air, or other mediums or surfaces using high intensity broad-spectrum pulsed light, high intensity pulsed light (HIPL), high intensity broad-spectrum pulsed light (BSPL), or pulsed white light (PWL) at a predetermined or tunable pulse rate, frequency, fluence (radiant exposure), peak power, exposure time, and/or pulse width to eliminate, reduce, degrade, or render inert or nullify physical, chemical or microbiological contaminants. The present disclosure is also related to a smart system that may function an as IoT (internet of things) device. IoT is a system of interrelated computing devices, mechanical and digital machines provided with unique identifiers and the ability to transfer data over a network without requiring human-to-human or human-to-computer interaction.

BACKGROUND

Liquid treatment is a process that improves the quality of liquid to make liquid more acceptable for an intended use, i.e., for human consumption. Liquid treatment removes contaminants and other undesirable components, or reduces the concentration of those contaminants and undesirable components or renders such undesirable or harmful components inert so that the liquid becomes fit for the intended use.

Treatment for potable and non-potable liquid production involves the removal of contaminants from raw liquid to produce liquid that is pure enough for human consumption. The destruction of physical, chemical, biological and microbiological contaminants, essential for prior to consumption and/or expulsion/disposal, very commonly involves the use of reactive chemical agents. However, residual chemical agents in such treated liquid may cause illness or even death. In some non-chemical liquid treatment systems, mercury may be used, which may cause environmental damage. In traditional light based liquid treatment systems, the high consumption of energy and high floor space requirement have proven to be less efficient.

Known methods and systems for clearing liquid (e.g., reducing turbid of liquid), e.g., reverse osmosis and membrane systems, consume excessive energy and lack robust reliability because microbiological organisms evolve, requiring tracking of known microbiological organisms as they evolve. As a result, known liquid filtration technologies may not adequately remove most microbiological contaminants. Further, known filtration technologies (e.g., reverse osmosis) waste resources, including energy, money, and even liquid. For example, for every gallon of liquid treated with reverse osmosis, about three-fourths is wasted.

A non-chemical, non-mercury, scalable liquid treatment system and method with low cost and reliable liquid production is desired. Traditional light based sterilization methods are typically large in size and expensive and reserved for very specific use cases.

SUMMARY

In at least one example embodiment, a scalable liquid, air, or surface treatment system using pulsed light to eliminate, reduce, degrade, or render inert or nullify physical, chemical, or microbiological contaminants includes a reactor having a liquid inlet, a liquid outlet, and an light source disposed between the liquid inlet and the liquid outlet. The system also includes at least one power supply to power the light source of the reactor, an ionized wire wrapped outside the light source of the reactor, at least one digital multiplexer connected to the at least one power supply, and a controller to control the light source to strobe pulsed light with a predetermined pulse rate, pulse width, fluence (energy flux density), frequency, and/or peak power. The controller is to further control the at least one digital multiplexer to power the light source to strobe pulsed light to reduce the contaminants at a molecular level.

In at least one example embodiment, the light source includes a non-mercury (e.g., a Xenon ultraviolet) flash lamp to generate the pulsed light.

In at least one example embodiment, the reactor includes an enclosure having a first end and a second end, a first outer cap housing the first end of the enclosure, and a second outer cap housing the second end of the enclosure. The first outer cap and the second outer cap are made of light (e.g., ultraviolet) resistant plastic to provide electrical insulation for the enclosure.

In at least one example embodiment, the enclosure includes a stainless steel shell. The stainless steel shell is to provide passive cooling to the liquid flow and to provide reflection of the light strobed by the light source.

In at least one example embodiment, the first end of the enclosure includes a first inner cap, and the second end of the enclosure includes a second inner cap. The first inner cap and the second inner cap are made of stainless steel and provide passive cooling to the liquid flow. The first inner cap is fluidly connected to the liquid inlet, and the second inner cap is fluidly connected to the liquid outlet.

In at least one example embodiment, the reactor further includes at least one containment quartz tube. The first inner cap is connected to a first end of the tube utilizing e.g., either of a press fit or interference fit. The second inner cap is connected to a second end of the tube utilizing e.g., either of a press fit or interference fit.

In at least one example embodiment, the light source is disposed within the tube, and the tube is disposed within a stainless steel shell of the enclosure.

In at least one example embodiment, the reactor includes bronze or copper to disinfect the liquid flow.

In at least one example embodiment, the liquid inlet and the liquid outlet are disposed near a bottom or a top of the reactor to facilitate liquid flow regulation and heat sinking.

In at least one example embodiment, the controller is to increase or decrease the pulse rate based on an increased or decreased liquid flow rate.

In at least one example embodiment, the system further includes at least one sensor to sense a pulse energy of the pulsed light at several points. The output from the sensor(s) is obtained by the controller which may vary the power/energy of the pulsed light, e.g., increase the power/energy if the sensed energy is lower than the predetermined energy threshold and decrease the power/energy if the sensed energy is higher than the predetermined energy threshold, to ensure sterilization using the required/predetermined pulsed light energy (with a desired safety factor).

In at least one example embodiment, pulse rate of the light is also tunable depending on system power consumption limitations. For example, the controller may decrease the power/energy of the pulsed light if a system's power consumption limit has been reached or if a threshold value before the power consumption limit has been reached.

In at least one example embodiment, the system also includes a filter to filter out contaminants from the liquid flow before the liquid flow enters a liquid inlet.

In at least one other example embodiment, a method of using pulsed light to eliminate, reduce, degrade, or render inert or nullify physical, chemical or microbiological contaminants in a liquid flow includes powering, by at least one power supply, a light source of a reactor via at least one digital multiplexer connected to the at least one power supply. The reactor includes a liquid inlet, a liquid outlet, the light source disposed between the liquid inlet and the liquid outlet, and an ionized wire is wrapped outside the light source of the reactor. The method also includes a controller controlling the light source to strobe pulsed light at a predetermined pulse rate, pulse width, fluence, frequency, and/or peak power to reduce the contaminants in the liquid flow at a molecular level.

In at least one example embodiment, the light source includes a non-mercury (e.g., Xenon ultraviolet) flash lamp (e.g., a 10 watt lamp). Thus, the method may further include the flash lamp generating the pulsed light.

In at least one example embodiment, the reactor includes an enclosure having a first end and a second end, a first outer cap housing the first end of the enclosure, and a second outer cap housing the second end of the enclosure. The first outer cap and the second outer cap are made of light (e.g., ultraviolet) resistant plastic to provide electrical insulation for the enclosure.

In at least one example embodiment, the enclosure includes a stainless steel shell, which may provide passive cooling to the liquid flow and further provide reflection of the pulsed light strobed from the light source.

In at least one example embodiment, the first end of the enclosure includes a first inner cap, the second end of the enclosure includes a second inner cap. The first inner cap and the second inner cap are made of stainless steel to provide passive cooling to the liquid flow. The first inner cap is fluidly connected to the liquid inlet, and the second inner cap is fluidly connected to the liquid outlet.

In at least one example embodiment, the reactor further includes at least one containment quartz tube, the first inner cap is connected to a first end of the tube by press fit or interference fit, and the second inner cap is connected to a second end of the tube by e.g., press fit or interference fit.

In at least one example embodiment, the light source is disposed within the tube, and the tube is disposed within a stainless steel shell of the enclosure.

In at least one example embodiment, the method also includes the controller increasing or decreasing the pulse rate based on an increased or decreased liquid flow rate.

It will be appreciated that the above embodiments are merely illustrative of the technical concept and features of liquid, air, or surface treatment with pulsed light, and these embodiments are to make a person skilled in the art understand the contents of the treatment system and to implement the treatment system without limiting the scope of protection of the treatment system. Any features described in one embodiment may be combined with or incorporated/used into the other embodiment, and vice versa. The equivalent change or modification according to the substance of the treatment system should be covered by the scope of protection of the treatment system.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

The present disclosure provides a detailed and specific description that refers to the accompanying drawings. The drawings and specific descriptions of the drawings, as well as any specific or alternative embodiments discussed, are intended to be read in conjunction with the entirety of this disclosure. The liquid, air, or surface treatment system may, however, be embodied in many different forms and should not be construed as being limited to the embodiments set forth herein; rather, these embodiments are provided by way of illustration only and so that this disclosure will be thorough, complete and fully convey understanding to those skilled in the art.

References are made to the accompanying drawings that form a part of this disclosure and which illustrate embodiments in which the systems and methods described in this specification may be practiced.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a", "an" and "the" include plural references unless the context clearly dictates otherwise. Although any systems and methods similar or equivalent to those described herein may be used in the practice or testing of embodiments of the present disclosure, the preferred systems and the preferred methods are now described.

It will be appreciated that embodiments disclosed herein use high intensity broad-spectrum pulsed light, high intensity pulsed light (HIPL), high intensity broad-spectrum pulsed light (BSPL), or pulsed white light (PWL), etc., and these types of light hereinafter are referred to as "light" or "pulsed light". A broad use case (e.g., liquid, air, and surface sterilization method) with affordability is desired for, e.g., to sterilize high contact surfaces from viruses, bacteria and other harmful substances during pandemic times.

Embodiments of the present disclosure will be described more fully hereafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Liquid treatment typically includes three treatment levels: primary level, secondary level, and tertiary level. Primary level liquid treatment focuses on removing visible elements unfit for consumption from the liquid. Secondary level liquid treatment focuses on removing sediments unfit for consumption (elements that are granular), typically using chemicals or other processes. Tertiary level liquid treatment removes heavy metals and/or microbiological contaminants like *e-coli, streptococcus*, or other non-visible elements from liquid using for e.g. reverse osmosis, ultra-filtration, nano-filtration, chlorination, ionization, absorption, etc. Embodiments disclosed and recited herein facilitate low energy consumption, chemical-free, mercury-free (e.g., no mercury in the lamps, non-mercury light), scalable liquid treatment system with pulsed light for reducing or even eliminating biological contaminants (including chemicals, perfluorooctanoic acid, etc.).

Embodiments disclosed herein eliminate elements in liquid on the scale of microns (e.g., at or under 50 microns) in size. The strobing/flashing of light in the embodiments disclosed herein, in contrast to constant light, cuts consumption of electricity because the light is pulsed periodically at a certain pulse rate with a certain pulse width. As a result of the light flashing facilitated by one or more of the embodiments described and recited herein, the structures (e.g., cell membrane, protein structure, and deoxyribonucleic acid, etc.) of the biological contaminants are disrupted to such an extent that the biological contaminants are unable to repair themselves and thus are unable to regrow and/or mutate. Pulsed light (e.g., pulsed UV light) has strong germicidal/deactivation properties due to a photon flux which may target the cell membrane, protein structures, and/or the deoxyribonucleic acid (DNA) structure.

Embodiments disclosed herein may induce photochemical, photothermal and/or photophysical damage to pathogenic microorganisms, leading to cell death, as follows: Photochemical damage: The UV light portion of the pulsed light damages the DNA of bacteria by forming thymine dimers. Upon dimer formation, bacterial DNA cannot be unzipped for replication, and thus bacteria cannot reproduce. Photothermal damage: Localized heating of bacteria is induced by pulsed light due to the difference in the heating/cooling rate and absorption characteristics of the bacteria and the surrounding matrix. Thus, the bacterial cell acts as a local vaporization center and may lead to membrane destruction and cell wall rupture. Thermal stress leads to rupture of microbial cells especially at higher flux densities ($>0.5$ J/cm$^2$). Photophysical damage: Pulsed light is also expected to induce some physical disruption on microbial cellular structures due to the intermittent, high-intensity pulses. Researchers have observed cell wall damage, membrane rupture, cytoplasm damage, etc. in bacterial cells exposed to pulsed light, even when the temperature increase was negligible, suggesting that photophysical effects can play a vital role in microbial inactivation.

Further, embodiments disclosed and recited herein are not reliant upon chlorine in contrast to a constant light system that dopes liquid with chlorine to prevent re-growth or mutation.

Embodiments disclosed and recited herein use pulsed light at different frequencies (or frequencies ranges) to reduce quantities of, or even eliminate altogether, different contaminants in liquid (flowing through the liquid treatment system) so that the microbiological contaminants, the liquid turbidity, the hydrocarbons the biochemical oxygen demand, the chemical oxygen demand, and/or the perfluorooctanoic acid is reduced/removed in one pulsed light process facilitated by a reactor as disclosed herein. Embodiments disclosed and recited herein may reduce or eliminate contaminants. Contaminants may include physical, chemical, biological, microbiological, and/or radiological contaminants. For example, contaminants may include e.g., microbiological contaminants (viruses, bacteria, etc.) such as *E-coli, Cryptosporidium*, CoV2, etc.; water turbidity; TSS (total suspended solids); PFOA's (perfluorooctanoic acid); TOC (total organic carbon); COD (chemical oxygen demand); BOD (biochemical oxygen demand); contaminants such as hydrocarbons; chemical contaminants—contaminants such PFAs (Per- and polyfluoroalkyl substances), munition compounds such as RDX (Research Department eXplosive) and DNAN (2,4-Dinitroanisole), pharmaceuticals such as CIP (ciprofloxacin) and TTC (tetracycline), and/or pesticides, etc.

Figure 1A:
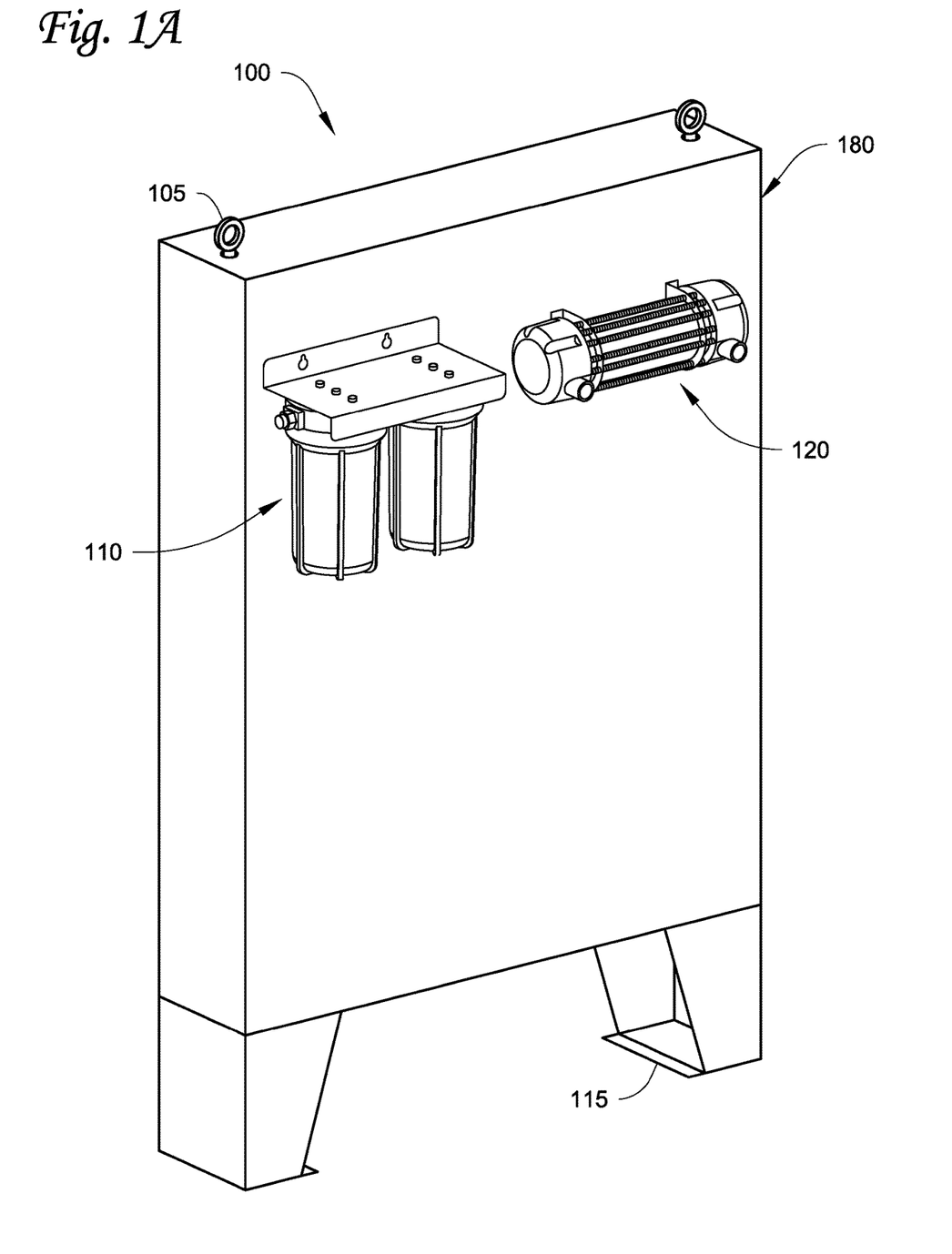
FIGS. 1A-1C are structural schematic diagrams of a liquid treatment system viewed at different angles, according to at least one example embodiment described herein.
Figure 1B:
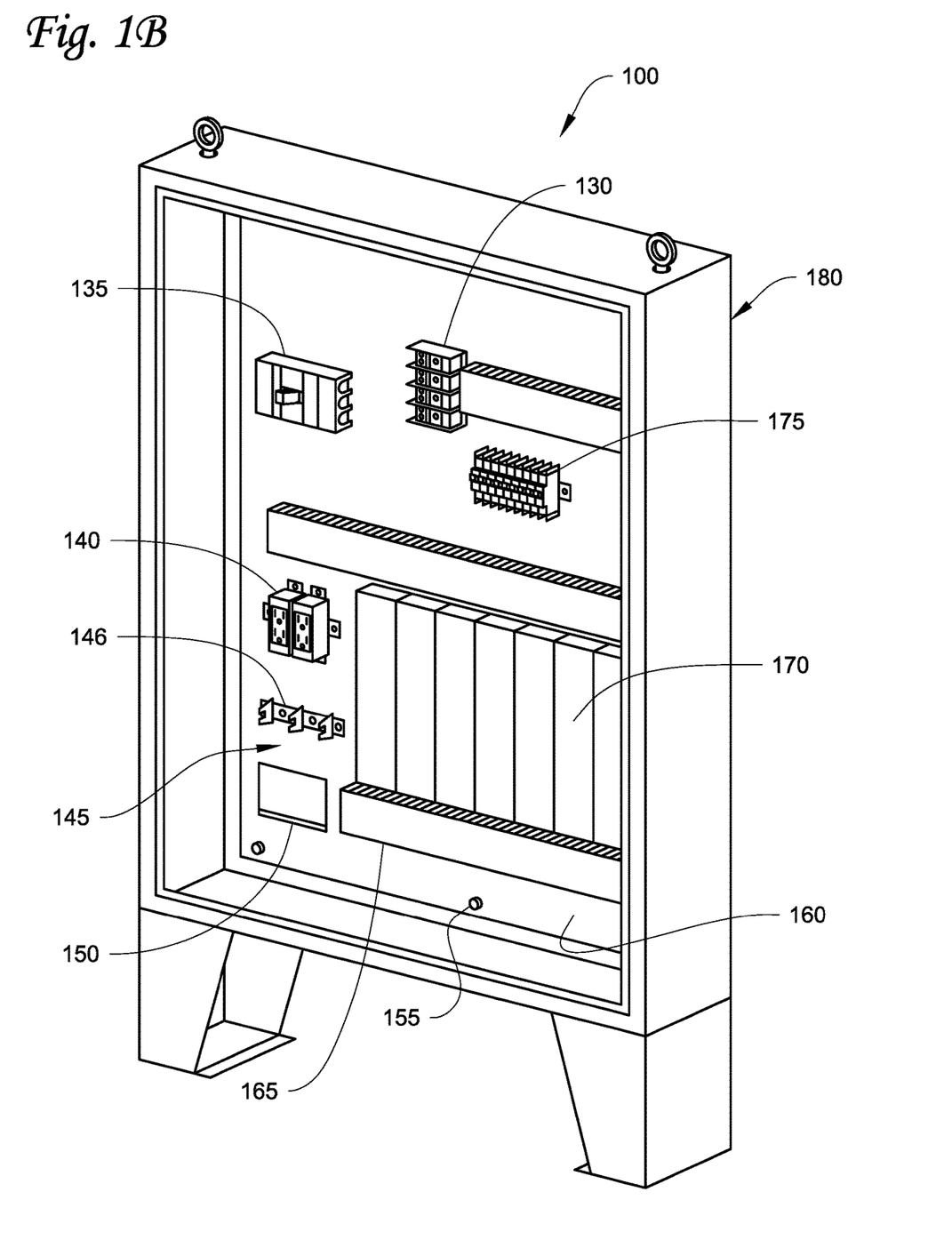
Figure 1C:
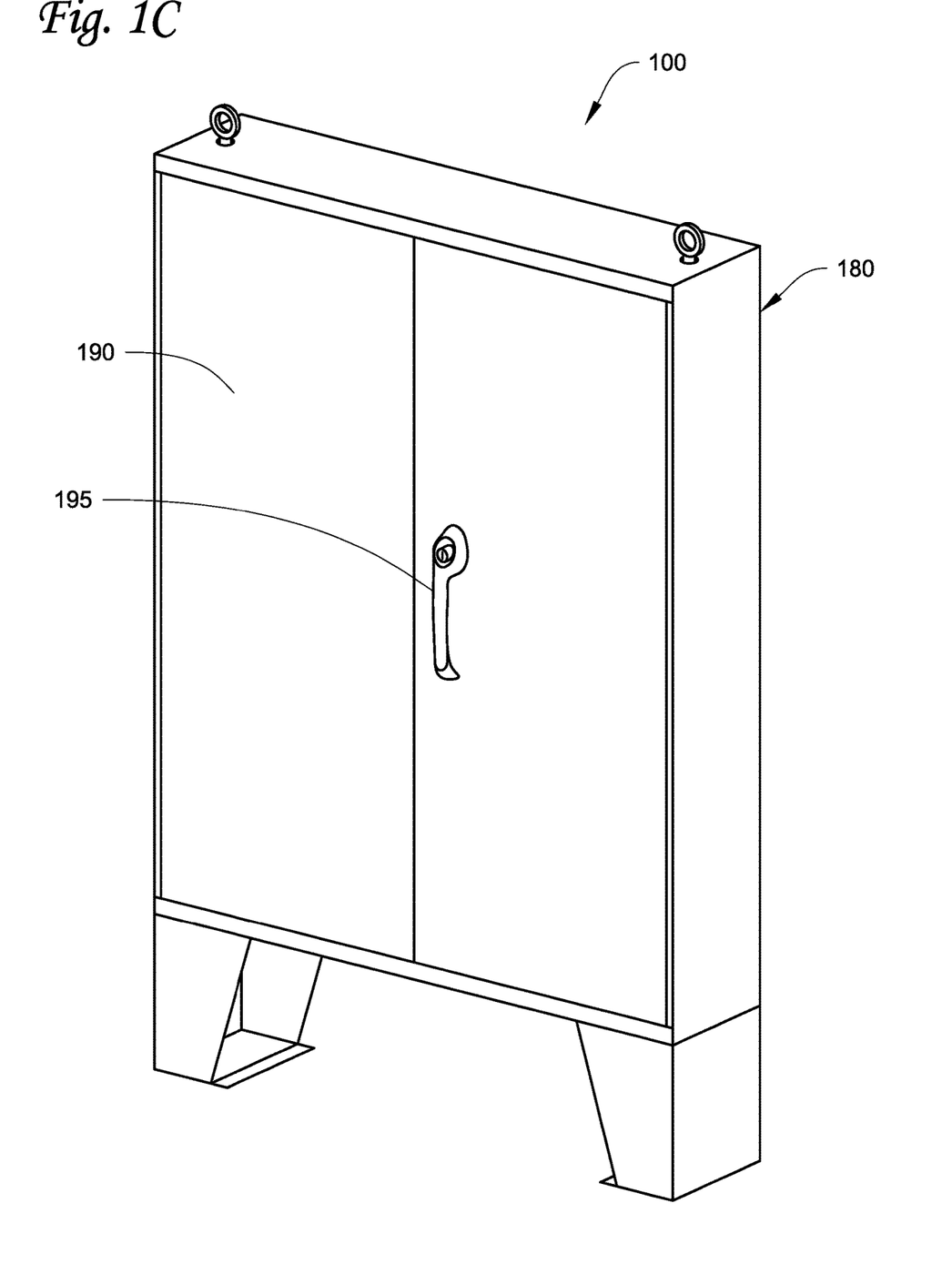

FIGS. 1A-1C are structural schematic diagrams of a liquid treatment system 100 viewed at different angles, according to at least one example embodiment described and recited herein.

The system 100 includes a housing 180, e.g., a sterilization housing or cabinet that houses electrical components of the system 100 and provides a mounting plane for the sterilization components (110, 120) of the system 100 on the reverse/back side of the housing 180. Example embodiments of the system 100 may be installed at a liquid filtration facility, at homes, in buildings, on ships, or next to a liquid source such as a stream, a river, or a lake, as non-limiting example environments.

The housing 180 may be installed outdoors or indoors and affixed (e.g., bolted) to a solid substrate to reduce or even eliminate movement. The housing 180 includes a lifting mechanism, e.g., moving bolt eyes, 105 that allows the system 100 to be mechanically lifted into place. In at least one non-limiting example embodiment, the system 100 has a weight at or about 400 lbs. It will be appreciated that the system 100, including housing 180, may be attached to moving objects and/or made hand-held.

The housing 180 also includes brackets, e.g., bottom bolting brackets, 115 facilitate mounting of the housing 180 onto the solid substrate to prevent movement of the housing 180. It will be appreciated that the housing 180 may be mounted onto the solid substrate using any other suitable mechanism such as clips, etc.

FIG. 1A shows a rear/back side of the housing 180, which includes, at least, a filter sub-system 110. In at least one non-limiting example embodiment, the filter sub-system 110 is a dual filtration (including two filters) system that is capable of receiving and treating liquid.

The system 100 may also include a reactor 120 that is connected to the filter sub-system 110. That is, the system 100 may include liquid pipe(s) to fluidly connect the filter sub-system 110 and the reactor 120. The system also includes connection assemblies having a connecting mechanism and a locking mechanism (such as bolt(s) and nut(s)) to mount the filter sub-system 110 and the reactor 120 on the back of the housing 180. The liquid pipe(s) and the connection assemblies are not shown. In at least one example embodiment, the filter sub-system 110 is optional.

In at least one example embodiment, the filter sub-system 110 is used to perform a first pass treatment of liquid by removing large contaminants from the liquid flow that passes into the system 120. In such embodiment, the sub-system 110 is disposed upstream of the reactor 120 relative to the liquid flow. The filter sub-system 110 may include one filter, two filters, or even no filters within the screw bases of the sub-system 110. In at least another example embodiment, the filter sub-system 110 is disposed downstream of the reactor 120. In at least another example embodiment, the sub-system 110 is disposed downstream of the reactor 120 relative to the liquid flow.

The reactor 120 sterilizes, disinfects and or/treats the liquid flow flowing through the reactor 120. In at least one example embodiment, the reactor 120 provides intense pulsed light to sterilize, disinfect and/or treat approximately 30 gallons of liquid per minute flowing through reactor 120. The embodiments herein are provided as examples only, and therefore other embodiments of reactor 120 are contemplated that are not limited to a volume of 30 gallons per minute.

The system 100 includes a circuit breaker 135. In at least one example embodiment, the circuit breaker 135 is Fuji Electric molded case circuit breaker (e.g., BW250 series) with parameters of 150 A, 600 VAC/250 VDC, 3-pole, thermal magnetic, 30 kA SCCR, 250 A frame, panel mount, etc. The circuit breaker 135 is the main input and a safety control subsystem of the system 100.

The system 100 also includes power rails 130 to distribute electrical power. In at least one example embodiment, the power rails 130 include three different segmentations, including hot, neutral, and ground, to provide breakout lines into each individual power unit/electrical component of the system 100.

The system 100 further includes outlets 140 that may include, e.g., Quad Din mounted outlets to provide individual duplex controlled outlets for internal control systems (e.g., at or about 120 volts system such as the control system 145) independent to the power supplied (e.g., 170) for the sterilization subsystem (110, 120). That is, the control system has a power supply (and outlets 140) independent of the power supplied to the sterilization subsystem (110, 120) because the sterilization subsystem (110, 120) has specific power supply distribution specifications and outlets for strobing/flashing. In at least one example embodiment, the external power supply (not shown) for the control system and/or the sterilization subsystem (110, 120) is shore power/utility power (e.g., 100-240 volts, etc.).

The system 100 also includes a control system 145. In at least one example embodiment, the control system 145 includes one or more processing boards having a controller 146/processor (e.g., an ARM processor) running control algorithm allowing individual digital multiplex (DMX) control of each of the components of the system 100 through, e.g., a control algorithm which may include for e.g., deep learning, machine learning and/or artificial intelligence systems.

The system 100 further includes an input/output device 150 that may be a touch-screen interface screen connected to the controller 146 of the ARM processing boards of the control system 145 to facilitate control (e.g., by a user) of the control system 145. It will be appreciated that access/control to the controller 146 may be remote via, e.g., through a web browser, a mobile app, etc.

The system 100 includes connector(s) (e.g., bolt(s)) 155 fixed on a panel 160 of the housing 180, allowing components inside the housing 180 and disposed on the metal panel 160 of the housing 180 to be removed for either repair or replacement.

The system 100 also includes wire raceways 165 that run wires between different components of the system 100 within the housing 180.

The system 100 further includes a power system 170 that may be an individual flash power system, e.g., at or around 20 ampere current, with DMX input/output to control each lamps of the reactor 120 by, e.g., the controller 146 of the control system 145. It will be appreciated that the power system 170 may be a flash power system and may include a DMX input(s)/output(s) to control each lamps of the reactor 120 on a one-to-one, one-to-multiple or multiple-to-multiple basis by, e.g., the controller 146 of the control system 145. For example, the power system 170 may control one or more lamps to flash individually or together with varying duration, intensity, etc.

In at least one example embodiment, the controller 146 controls the DMX of the power system 170, by e.g., executing a control software. The control can be manual (e.g., via a user command through the input/output device 150), predetermined (e.g., with preset values of the DMX control parameters), or dynamic (adjusted based on current conditions such as available input power, liquid flow rate, etc.). The controller 146 controls the DMX to control or synchronize the power supplied to the lamps of the reactor 120 on a one-to-one, one-to-multiple, or multiple-to-multiple basis. The power/energy supplied to the lamp(s) of the reactor 120 is the amount of intensity (or irradiance, duration, energy density, or dose, etc.) to flash the lamp(s) in the reactor 120.

The system 100 also includes a circuit breaker 175 that may be an Eaton miniature circuit breaker (current-limiting, 20A, Din mountable unit, etc.). The circuit breaker 175 is a secondary shutoff system that allows a single component of the system 100 to fail without causing the entire system 100 to fail, and further allows individual components of the system 100 to be powered down.

The components 130, 135, 140, 145, 150, 155, 160, 165, 170, and 175 of the system 100, described above, may be disposed in the interior of the housing 180. It will be appreciated that the system also includes at least two power supplies (e.g., one to power the control system 145 and one to power the reactor 120), electrical power lines, and control lines to connect those components listed above, including sub-system 110 and reactor 120, to provide power thereto and to provide control by the controller 146. The electrical power lines and the control lines are not shown.

The housing 180 also includes front panel(s) (e.g., door(s)) 190 to cover the housing 180 and an opening/locking mechanism 195 to open/close/lock the panel(s) 190 of the housing 180.

Figure 2A:
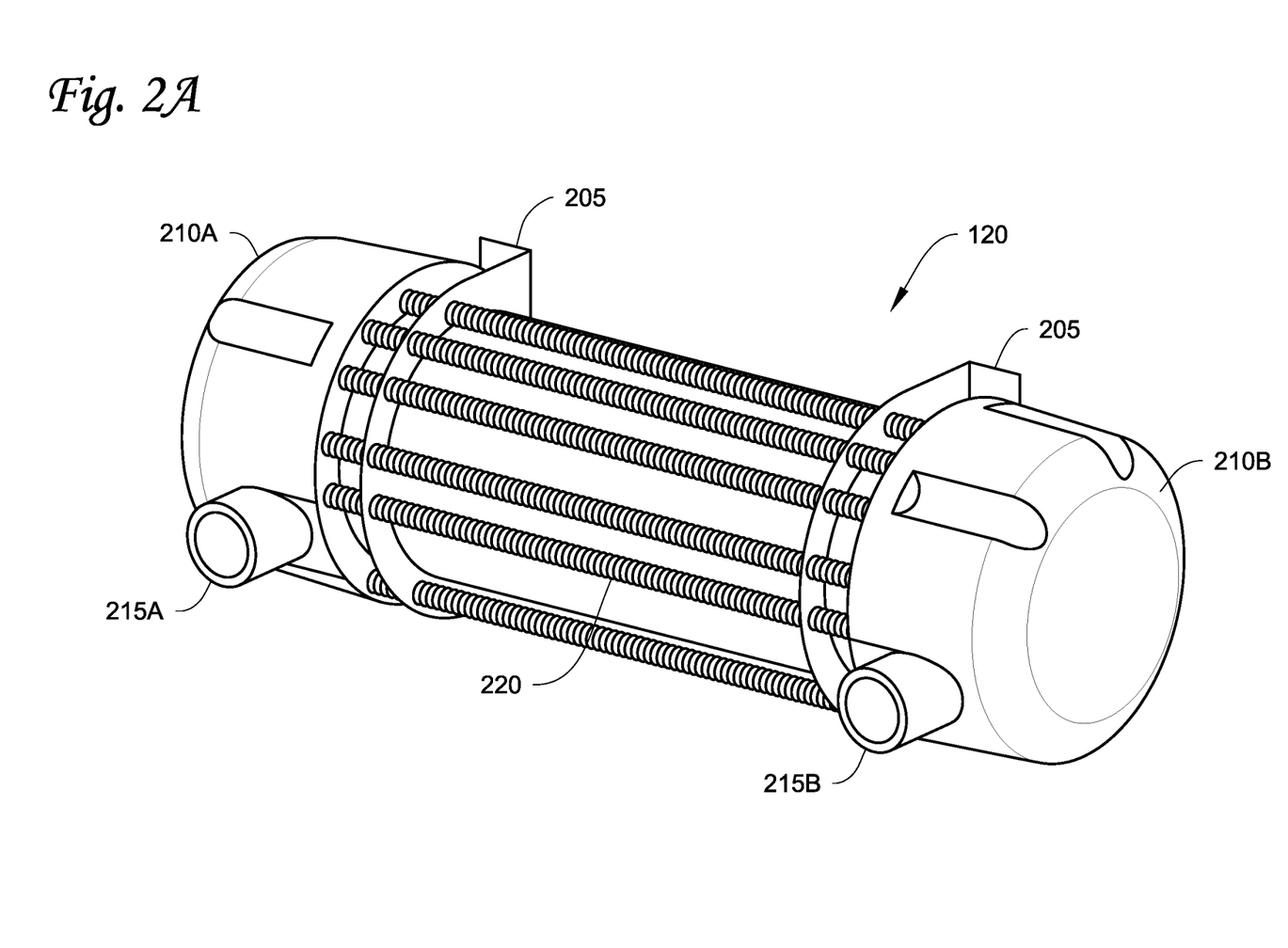
FIGS. 2A and 2B are structural schematic diagrams of a reactor of a liquid treatment system viewed at different angles, according to at least one example embodiment described herein.
Figure 2B:
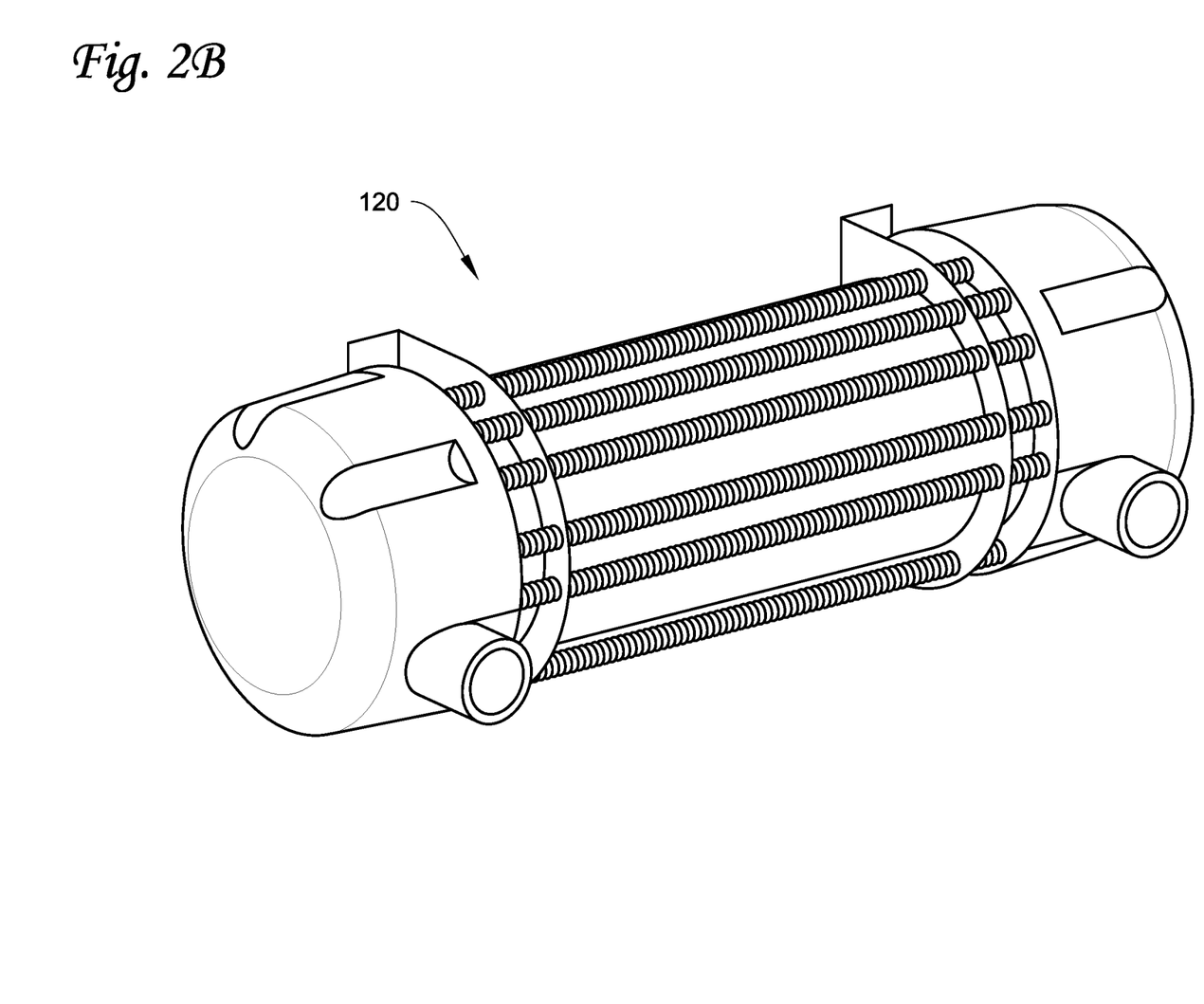
Figure 2C:
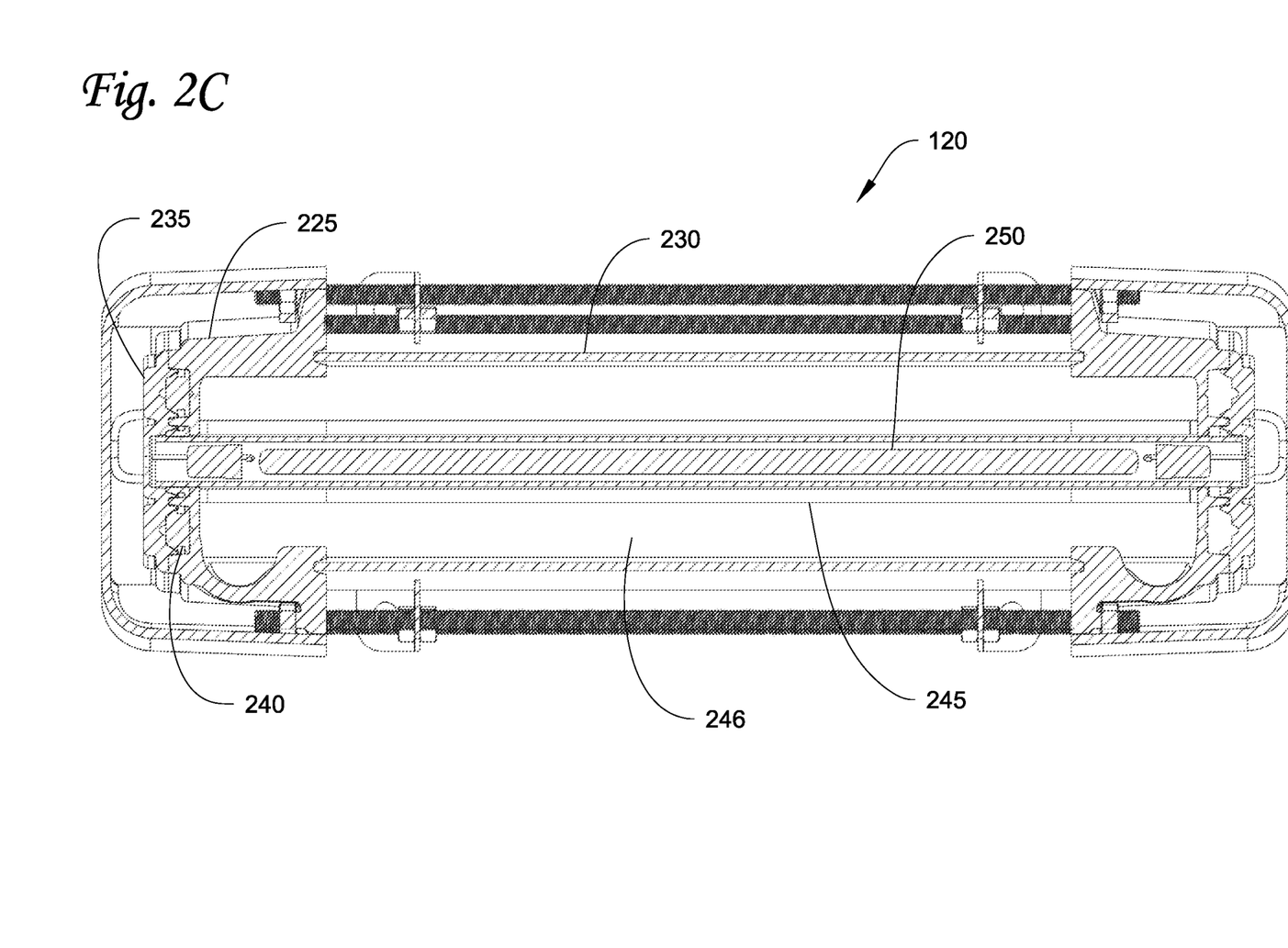
FIG. 2C is a cross sectional view of the reactor of FIGS. 2A and 2B, according to at least one example embodiment described herein.

FIGS. 2A and 2B are structural schematic diagrams of a reactor 120 of a liquid treatment system viewed from different angles, according to at least one example embodiment described herein. FIG. 2C is a cross sectional view of the reactor 120 of FIGS. 2A and 2B, according to at least one example embodiment described herein.

The reactor 120 includes a liquid inlet/outlet 215A and a liquid outlet/inlet 215B. In at least one example embodiment, the inlet/outlet 215A, 215B includes a circular port to facilitate the intake and output of liquid to and from the reactor 120. As a non-limiting example, the circular port may have a diameter of % of an inch. It will be appreciated that the system 100 overall may cover all aspects of a smart system (which may include reactor 120) that could function an as IoT (internet of things) device.

The reactor 120 also includes two outer caps 210A, 210B. In at least one example embodiment, the outer caps 210A, 210B are made of light (e.g., UV) resistant plastic to safeguard/house an enclosure of the reactor 120, to provide electrical insulation for the enclosure of the reactor 120, and to provide protections to the enclosure of the reactor 120.

The reactor 120 further includes rods 220 that, in at least one example embodiment, may be threaded to allow the components of the reactor 120 to be compressed together at a desired/optimal/predetermined torque. In one example embodiment, the predetermined torque may be at or around 7 foot-pounds. In at least one example embodiment, there are a plurality of rods 220 arranged around a parameter of the enclosure of the reactor 120.

The reactor 120 also includes brackets 205 that facilitate mounting of the reactor 120 to the back of the housing, e.g., the housing 180, for sturdy positioning while in use.

The enclosure of the reactor 120 includes a shell 230. The enclosure of the reactor 120 also includes a compression plate 235 at opposite ends of the reactor 120. In at least one example embodiment, a compression plate 235 is a stainless steel compression plate that compresses rubber gaskets around the outer parts of the quartz tubes 245 to provide a liquid tight seal. An internal space 246 is formed between the shell 230 and the quartz tubes 245 to allow liquid to pass through from inlet (215A, 215B) to outlet (215B, 215A).

The enclosure of the reactor 120 includes an inner cap 225 at opposite ends of the reactor 120. In at least one example embodiment, the inner cap 225 is a stainless steel cap that interlocks into the shell 230. Each inner cap 225 acts as a passive cooling system for the liquid flow. Each cap 225 connects to a liquid inlet or outlet such that liquid enters the reactor 120 turbulently and/or maintains turbulence. The turbulence causes the liquid to stay in the space 246 longer and disturbs the liquid to prevent shadowing. In at least one example embodiment, the cap 225 has the liquid inlet/outlet (intake/outtake nozzles) built-in to increase turbulence within the space 246. The quartz tube 245 which may be, in at least one embodiment, medical grade piping. It will be appreciated that quartz tube can be resistant to e.g., ultraviolet light. When turbulence is created in the liquid flow, the liquid flow moves so that bacteria cannot hide from the pulsed light. It will be appreciated that there may be a curve between each cap and a liquid inlet or outlet to cause the liquid turbulence in a circular motion. Liquid turbulence may be created by pushing liquid through a bottom of the reactor 120 and liquid exiting from a top through a liquid pipe. Liquid turbulence may also be created by liquid being pushed through a top of the reactor 120 and exiting from the bottom through a liquid pipe. In one example embodiment, the liquid turbulence liquid flow rate is created at or around 30 gallons per minute.

In at least one example embodiment, there may be one to six or more treatment/sterilization tubes 245 built with corresponding internal flash lamps 250, each individually controllable by the controller 146 and contained within individual quartz tubes 245 that are housed within a compression-held stainless steel enclosure of the reactor 120. The containment quartz tubes 245 provide greater light resistance to "clouding" from the lamps 250.

The reactor 120 includes at least one, e.g., one to six, light source 250 that is a replaceable non-mercury (e.g., Xeon UV) flash lamp. The light source 250 is powered by a power supply of the system 100 along with the components (e.g., 130, 135, 165, 170, 175 of FIG. 1B) of the system 100. The controller 146 of the control system (e.g., 145 of FIG. 1B) controls the light source 250 to strobe/flash light at a predetermined pulse rate, a predetermined exposure time, a predetermined frequency (e.g., a predetermined light frequency/spectrum/wavelength), a predetermined peak power/energy, a predetermined fluence, and/or a predetermined pulse width/duration. In at least one example embodiment, the controller 146 controls the light source 250 to strobe/flash light at a predetermined fluence, a predetermined pulse rate, a predetermined pulse width, a predetermined frequency, and a predetermined peak power. In at least one example embodiment, the predetermined pulse rate/frequency of the strobe light ranges from at or around 0 to at or around 100 pulse per second (e.g., six flashes simultaneously over at or about 1.3 seconds) or ranges from at or around 0 HZ to at or around 60 Hz (or from at or around 5 Hz to at or around 1000 Hz); the predetermined fluence is at or around 10 mJoule/cm2 (or at or around 500 mJoule/cm2) to at or around 5000 Joule/cm2 or higher as needed (over a predetermined exposure time or pulse width which ranges from at or about 0.1 picosecond to at or about 10 seconds such as at or about 1.3 seconds) based on at or around 100 volts or at or around 240 volts voltage; the predetermined light spectrum (e.g., wavelength of the light) is at or around 0.1 nm to 1500 nm; and the predetermined peak power/energy is at or about 10 watts in three milliseconds. It will be appreciated that the exposure time (treatment time) is the time when liquid is in the space 246. In at least one example embodiment, the light source 250 is enveloped in the quartz tubes 245 where the liquid flows through the space 246 outside of the quartz tubes 245. In at least one example embodiment, the controller 146 controls the power supply and/or the light source to turn the power of the light source on and then off, e.g., 5 times/flashes per second, 10 times/flashes per second, 100 times/flashes per second, or once every 1 to 10 seconds, once every three milliseconds etc. It will be appreciated that the power supplied to the electrical components of the system 100 can be alternating current and/or direct current power.

It will be appreciated that by strobing/flashing light at a predetermined pulse rate, fluence, peak power/energy, frequency, and/or pulse width, etc. to a liquid flow, the physical, chemical or microbiological contaminants may be eliminated, reduced, degraded, or rendered inert or nullified. Strobing/flashing light at a predetermined pulse rate, fluence, peak power/energy, frequency, and/or pulse width, etc. also eliminates/eradicates/removes contaminants from a surface, in air, in other medium, etc. That is, embodiments disclosed herein are applicable to air and/or surface sterilization, disinfection and/or treatment in addition to liquid flow. It will also be appreciated that for air and/or surface sterilization, disinfection and/or treatment, the lamps 250 may serve as the reactor itself (i.e., the enclosure, the shell 230, and/or the tube 245, etc. can be optional) instead of being enclosed in the shell 230 and/or the tube 245.

Figure 2D:
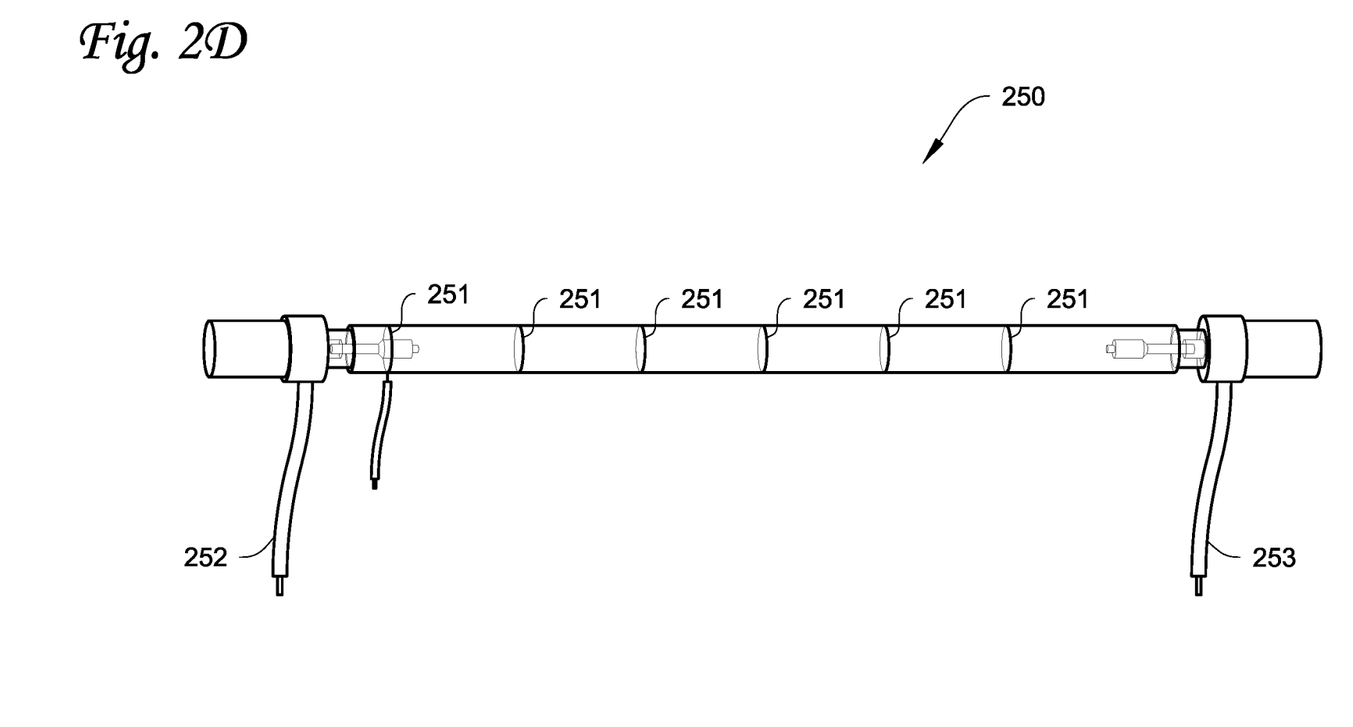
FIG. 2D is a structural schematic diagram of a wire wrapped outside of a light source, according to at least one example embodiment described herein.
Figure 3A:
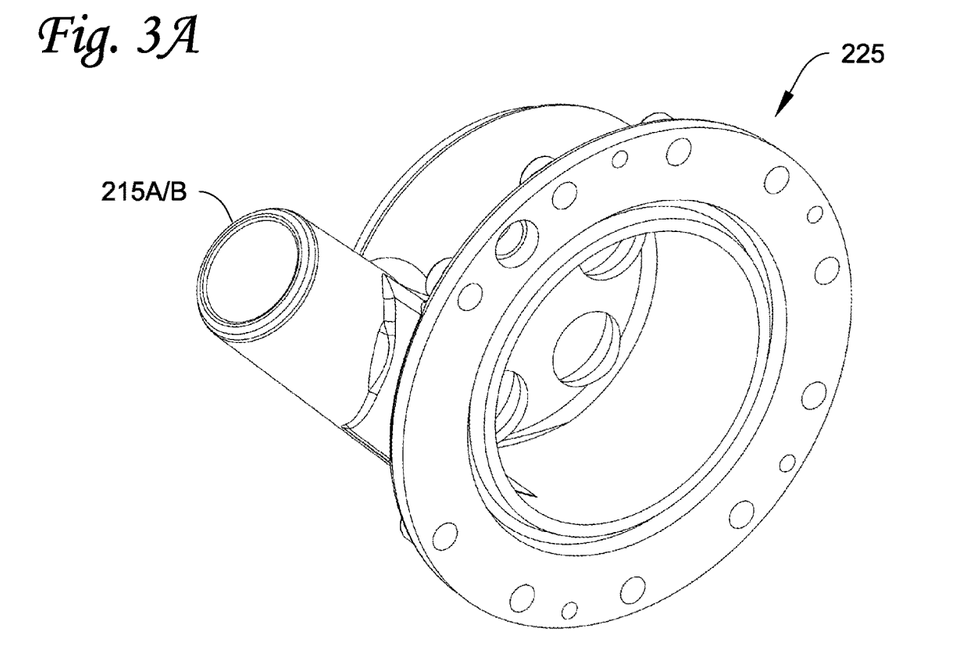
FIGS. 3A-3F are structural schematic diagrams of some components of a reactor, according to at least one example embodiment described herein.
Figure 3B:
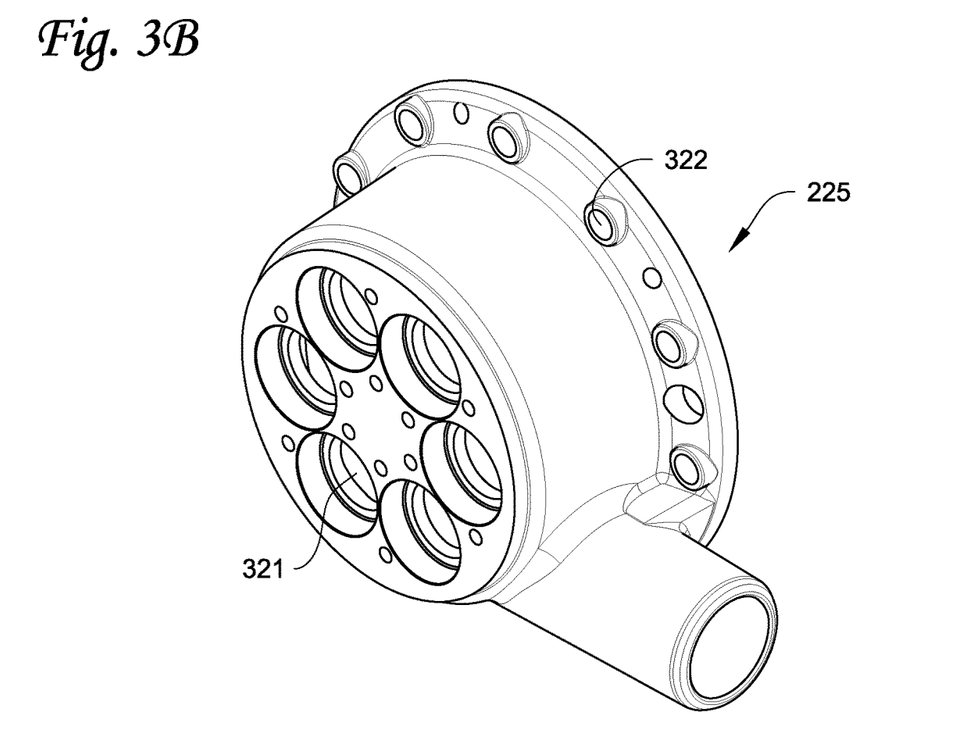
Figure 3C:
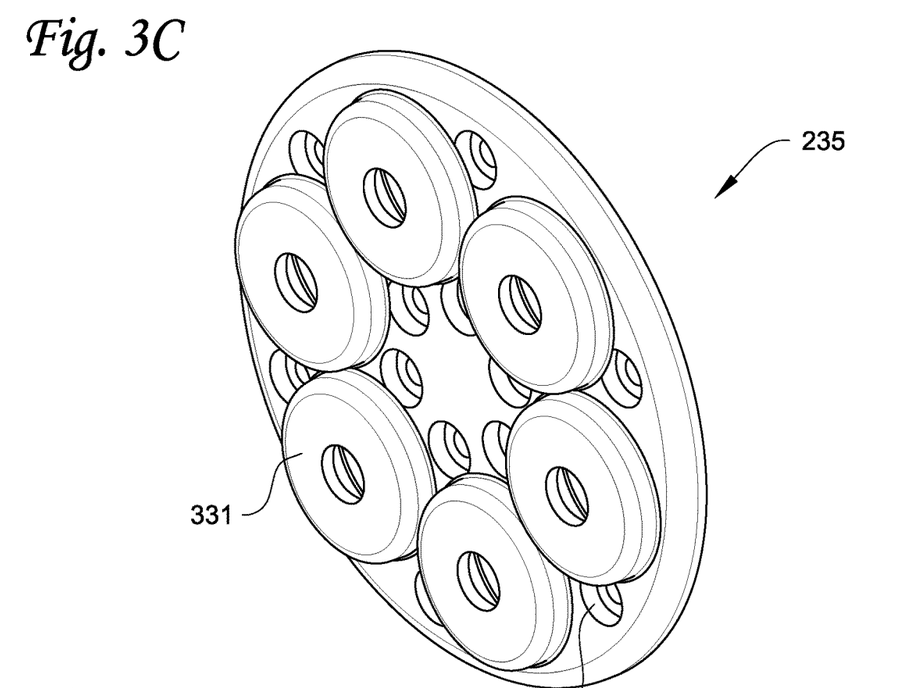
Figure 3D:
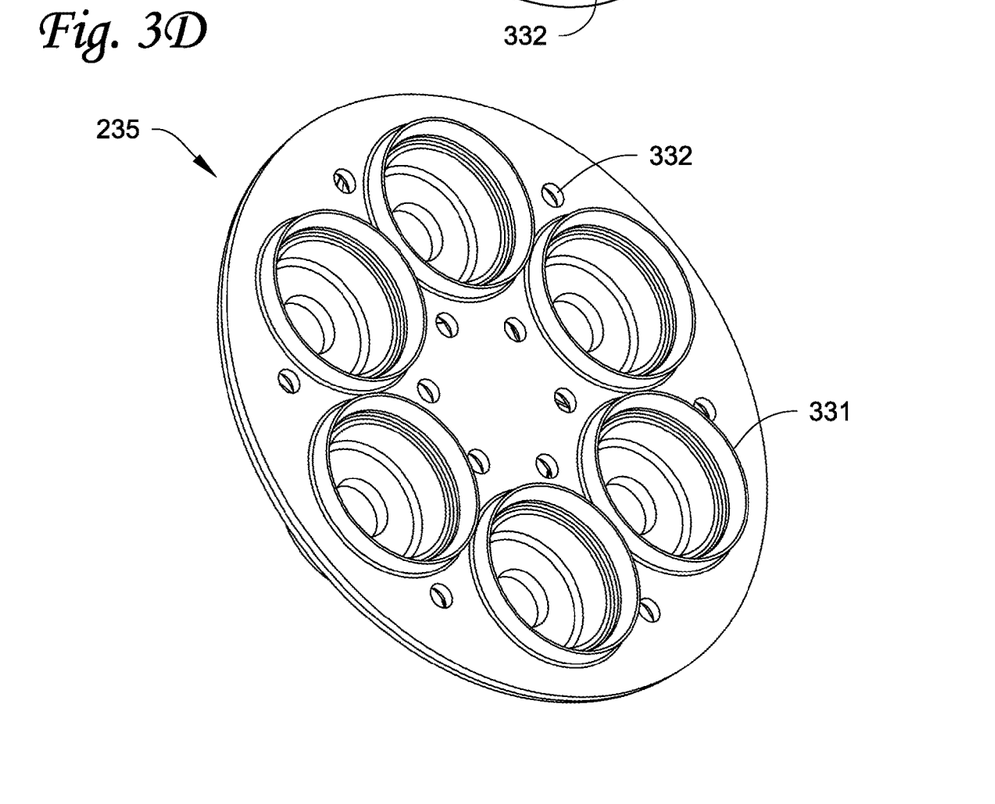
Figure 3E:
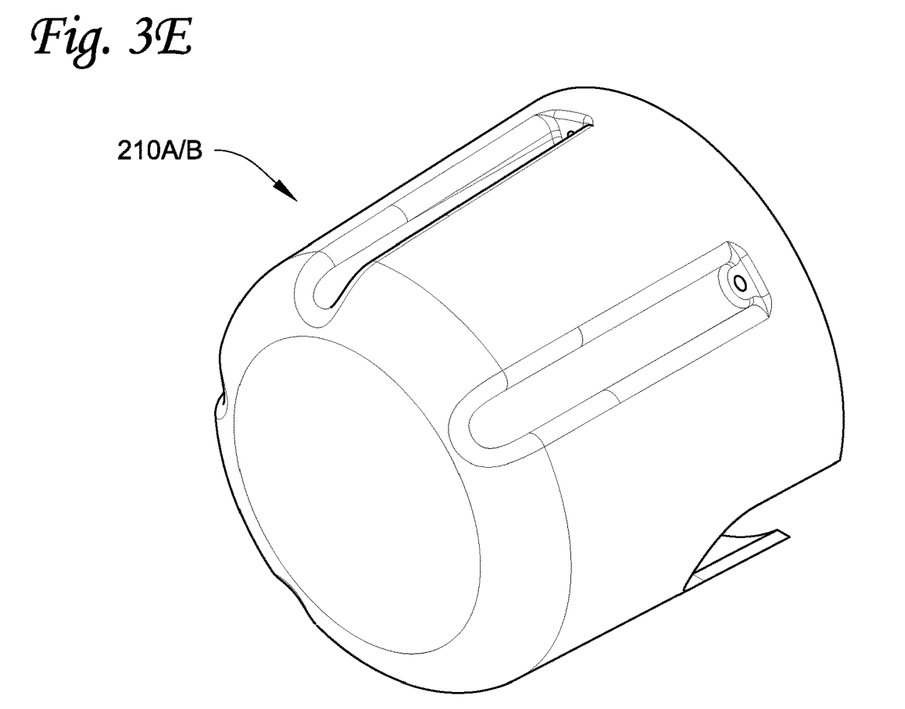
Figure 3F:
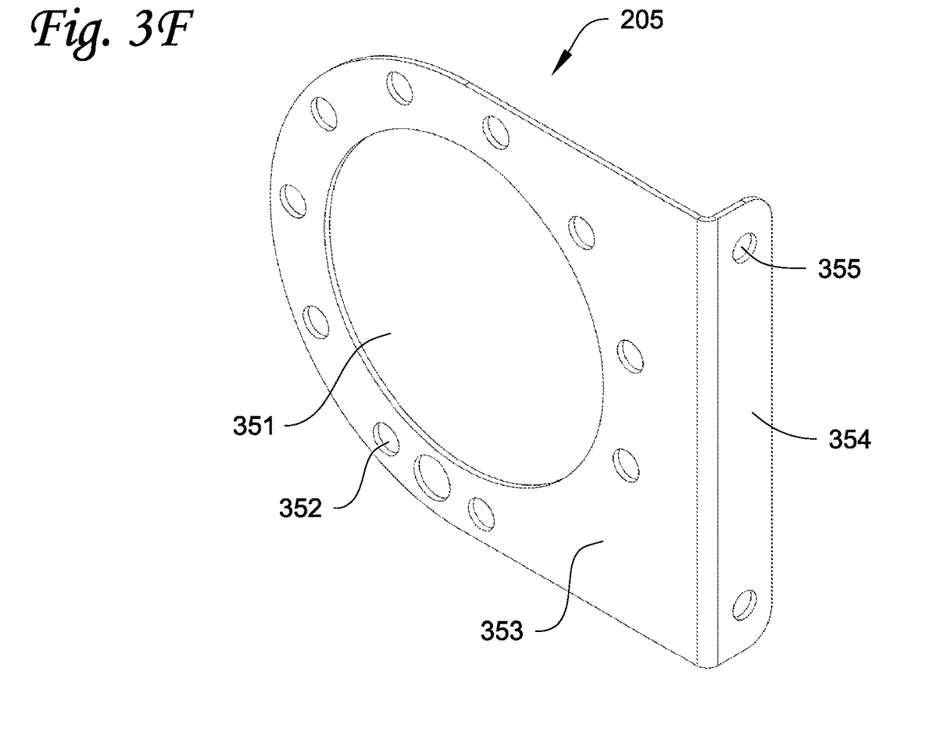

FIG. 2D is a structural schematic diagram of a wire 251 wrapped outside of a light source 250, according to at least one example embodiment described herein. A wire 251 may be disposed between the power system 170 (of FIG. 1B) and each of the light source(s) 250. In at least one example embodiment, the wire 251 may be an ionized/arc wire e.g. a mirror-finished tungsten wire. The ionized wire may be a wire type corona discharge electrode (e.g., made of tungsten) connected to the power system 170. The light source 250 of the reactor 120 may be e.g., a pulsed Xenon lamp. The light source 250 includes power lines 252 and 253 connected to the power system 170. The ionized wire 251 may be wrapped outside of the light source 250 of the reactor 120 (inside the tubes 245 of FIG. 2C), around the light source 250, and extending from one end of the light source 250 to the other end of the light source 250 with a predetermined distance between each wrap. It will be appreciated that the ionized wire 251 may make it easier to ignite the light source 250 (e.g., allowing to use less voltage to ignite the lamp(s) than a configuration without the ionized wire. Without the ionized wire, a lot of large capacitors (e.g., capacitors with large capacitance) or capacitor bank(s) may be required between the power system 170 and the lamp(s) to e.g., lower the resistance. It will be appreciated that with the ionized wire 251, only at or about a 100th or at or about a 1000th of the capacitance/capacitors may be required as compared to capacitance/capacitors required in the configuration without the ionized wire. With the ionized wire 251, the ionized wire may receive a high voltage through the wire 251 making a gap between the electrodes in the lamp easier to ignite and able to ignite with a voltage lower than the voltage required in the configuration without the wire. Without the ionized wire, a high current may be needed to overcome the spark gap than the current required in the configuration with the ionized wire 251.

It will further be appreciated that existing experiments with disinfection products to sterilize, disinfect and/or treat food etc., all create custom power supplies (instead of using utility/shore power) limiting the scalability, flexibility, and making it cost prohibitive.

Referring back to FIG. 2C, the reactor 120 also includes gaskets 240 that may be, e.g., rubber gaskets for expansion/sealing around the shell 230.

The enclosure of the reactor 120 also includes a shell 230 that may be a stainless steel shell to provide passive cooling along with additional reflection of the light provided from the internal lamps 250. In at least one example embodiment, the enclosure of the reactor 120 has a cylinder shape.

It will be appreciated that the components of the reactor 120 with passive cooling capability dissipate heat from the lamp 250. In the liquid treatment system 100, the liquid is a heat sink for the lamp 250 (Xenon lamp typically creates a lot of heat). Liquid flows up for flow regulation and heat sinking, so that there is no need to cool the lamp 250 separately. That is, when the liquid flows through the space 246, there is heat sinking into the liquid.

In at least one example embodiment, the controller 146 controls a switch (e.g., a knob, a switch, a software-based switch, etc.) for Class A, e.g., increased pulse rate, and Class B, e.g., decreased pulse rate, sterilization, disinfection and/or treatment modes may be included/connected to the controller 146. In at least another example embodiment, for a limited power supply, the system may perform variable flashing, for example, the controller 145 may decrease the pulse rate when the volume of liquid flowing through the system/reactor is less than a threshold value, e.g., decreased liquid flow rate, or increase the pulse rate when the volume of liquid flower through the system/reactor is equal to or greater than the threshold value, e.g., increased liquid flow rate.

FIGS. 3A-3F are structural schematic diagrams of some components of the reactor 120 of FIGS. 2A-2C, according to at least one example embodiment described herein.

In at least one example embodiment, the component 225 includes openings 322 for connection (e.g., for connecting bolts/pins/rods to pass through) and openings 321 for housing the end(s) of the tubes (e.g., tubes 245 of FIG. 2C).

In at least one example embodiment, the compression plate 235 includes gaskets 331 around the out parts of the quartz tubes. The compression plate 235 also includes at least one opening 332 connection for connecting bolts/pins/rods to pass through.

In at least one example embodiment, the bracket 205 includes openings 352 for connection (e.g., for connecting bolts/pins/rods to pass through), opening 351 for the enclosure of the reactor to pass through, a first plate 353, a second plate 354 having openings 355 so that the bracket 205 is mounted on the back of the housing 180 of FIG. 1A.

It will be appreciated that the designs of FIG. 3A-FIG. 3F may facilitate the quartz tube 245 being easily replaced (e.g., for maintenance purposes) without taking apart the reactor 120. For example, during maintenance, the end cap(s) can be removed and the quartz tube(s) 245 can be replaced.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Different features, variations and multiple different embodiments have been shown and described with various details. What has been described in this application at times in terms of specific embodiments is done for illustrative purposes only and without the intent to limit or suggest that what has been conceived is only one particular embodiment or specific embodiments. It is to be understood that this disclosure is not limited to any single specific embodiments or enumerated variations. Many modifications, variations and other embodiments will come to mind of those skilled in the art, and which are intended to be and are in fact covered by both this disclosure. It is indeed intended that the scope of this disclosure should be determined by a proper legal interpretation and construction of the disclosure, including equivalents, as understood by those of skill in the art relying upon the complete disclosure present at the time of filing.

The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality.

Specific examples of operably couplable include but are not limited to physically mateable and/or physically interacting components and/or wirelessly interactable and/or wirelessly interacting components and/or logically interacting and/or logically interactable components.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A liquid treatment system using high intensity broad-spectrum pulsed light to reduce physical, chemical, biological, or microbiological contaminants, the system comprising:
   a reactor having a shell, a liquid inlet, a liquid outlet, a plurality of tubes, and a plurality of light sources disposed between the liquid inlet and the liquid outlet, wherein each of the plurality of light sources is respectively contained within the plurality of tubes;
   an ionized wire wrapped outside each of the plurality of light sources of the reactor inside the plurality of tubes;
   at least one power supply to power the plurality of light sources of the reactor;
   at least one digital multiplexer connected to the at least one power supply; and
   a controller to:
      control the at least one digital multiplexer to power the plurality of light sources to strobe pulsed light with a predetermined fluence to treat contaminants,
   wherein the reactor further includes:
      an enclosure, the enclosure having a first end and a second end;
      a first outer cap housing the first end of the enclosure; and
      a second outer cap housing the second end of the enclosure,
      wherein the first end of the enclosure includes a first inner cap and the second end of the enclosure includes a second inner cap,
      wherein the first inner cap is fluidly connected to the liquid inlet, and the second inner cap is fluidly connected to the liquid outlet,
      wherein a portion of the first inner cap that is configured to receive the liquid and a portion of the second inner cap connected to the liquid outlet are curved and configured to create turbulence of liquid flow in a circular motion in the reactor, and
      wherein the plurality of light sources is provided concentrically around a center axis of the reactor in the shell such that an internal space is formed between the shell and the plurality of tubes such that liquid passes through the internal space in the circular motion between the shell and the plurality of tubes and between the plurality of tubes from the liquid inlet to the liquid outlet.

2. The system according to claim 1, wherein the plurality of light sources includes a non-mercury flash lamp to generate the pulsed light.

3. The system according to claim 1, wherein the first outer cap and the second outer cap are made of light resistant plastic to provide electrical insulation for the enclosure.

4. The system according to claim 1, wherein the shell is a stainless steel shell to provide passive cooling and to provide reflection of the pulsed light strobed by the plurality of light sources.

5. The system according to claim 3, wherein
   the first inner cap and the second inner cap are made of stainless steel to provide passive cooling.

6. The system according to claim 1, wherein:
   the plurality of tubes are containment quartz tubes,
   the first inner cap is connected to a first end of the plurality of tubes, and
   the second inner cap is connected to a second end of the plurality of tubes.

7. The system according to claim 1, wherein the reactor includes bronze or copper material to disinfect liquid flow.

8. The system according to claim 1, wherein the liquid inlet and the liquid outlet are configured to enable liquid flow regulation and heat sinking.

9. The system according to claim 1, wherein the controller is to increase or decrease the pulse rate based on an increased or decreased liquid flow rate.

10. The system according to claim 1, further comprising at least one sensor to sense an energy of the pulsed light.

11. The system according to claim 1, further comprising a filter to filter contamination from a liquid flow before the liquid flow enters the liquid inlet.

12. A method of reducing physical, chemical, biological, and microbiological contaminants, the method comprising:
   powering, by at least one power supply, a plurality of light sources of a reactor via at least one digital multiplexer connected to the at least one power supply,
      wherein the reactor includes a shell, a liquid inlet, a liquid outlet, a plurality of tubes, an enclosure, the enclosure having a first end and a second end, a first outer cap housing the first end of the enclosure, and a second outer cap housing the second end of the enclosure, wherein the first end of the enclosure includes a first inner cap and the second end of the enclosure includes a second inner cap, wherein the first inner cap is fluidly connected to the liquid inlet, and the second inner cap is fluidly connected to the liquid outlet, and the plurality of light sources disposed between the liquid inlet and the liquid outlet, and an ionized wire is wrapped outside each of the plurality of light sources of the reactor,
      wherein each of the plurality of light sources having the wrapped ionized wire is respectively contained within the plurality of tubes;
   creating turbulence of liquid flow in a circular motion in the reactor, wherein a portion of the first inner cap that is configured to receive the liquid flow and a portion of the second inner cap connected to the liquid outlet are curved, and
      wherein the plurality of light sources is provided concentrically around a center axis of the reactor in the shell such that an internal space is formed between the shell and the plurality of tubes such that the liquid flow passes through the internal space in the circular motion between the shell and the plurality of tubes and between the plurality of tubes from the liquid inlet to the liquid outlet;
   controlling, by a controller, the plurality of light sources to strobe pulsed light with a predetermined fluence to reduce physical, chemical, biological, or microbiological contaminants at a molecular level.

13. The method according to claim 12, wherein the plurality of light sources includes a non-mercury flash lamp, and the method further comprises:
 generating, by the flash lamp, the pulsed light.
14. The method according to claim 12,
 wherein the first outer cap and the second outer cap are made of light resistant plastic to provide electrical insulation for the enclosure.
15. The method according to claim 14, wherein the shell is a stainless steel shell, and the method further comprises:
 passively cooling, using the stainless steel shell, the reactor,
 reflecting, using the stainless steel shell, the pulsed light strobed from the plurality of light sources.
16. The method according to claim 14, wherein
 the first inner cap and the second inner cap are made of stainless steel to provide passive cooling.
17. The method according to claim 16, wherein:
 the plurality of tubes are containment quartz tubes,
 the first inner cap is connected to a first end of the plurality of tubes,
 the second inner cap is connected to a second end of the plurality of tubes.
18. The method according to claim 12, further comprising:
 increasing or decreasing, by the controller, the pulse rate based on an increased or decreased liquid flow rate.
19. The system according to claim 1, further comprising:
 a switch controlled by the at least one controller, wherein the switch is configured to switch between a first configuration and a second configuration, wherein in the first configuration, a pulse rate of the pulsed light is increased and in the second configuration, the pulse rate of the pulsed light is decreased, or
 wherein the switch is configured to switch is configured to switch between sterilization, disinfection, and treatment modes.

* * * * *